United States Patent [19]
Niino

[11] Patent Number: 6,007,876
[45] Date of Patent: Dec. 28, 1999

[54] METHOD FOR PRODUCING POLYMER ARTICLES WITH A SURFACE MODIFIED

[75] Inventor: Hiroyuki Niino, Tsukuba, Japan

[73] Assignee: Director-General of Agency of Industrial Science and Technology, Tokyo, Japan

[21] Appl. No.: 09/046,632

[22] Filed: Mar. 24, 1998

[30] Foreign Application Priority Data

Jan. 20, 1998 [JP] Japan .................................. 10-008144

[51] Int. Cl.⁶ ...................................................... C08F 2/48
[52] U.S. Cl. ........................ 427/508; 427/384; 427/554; 427/581
[58] Field of Search ................................... 427/508, 554, 427/581, 384

[56] References Cited

U.S. PATENT DOCUMENTS 5,013,660  5/1991  Kasuya et al. ........................... 435/173
5,582,955  12/1996  Keana et al. ............................. 430/296

FOREIGN PATENT DOCUMENTS 4-183873  6/1992  Japan .
7-5775B2  1/1995  Japan .
7-5777B2  1/1995  Japan .

OTHER PUBLICATIONS

I. Kaetsu, Nuclear Instruments And Methods In Physics Research, B105:294 (1995) (no month avail.).
Y. Li et al., J. Appl. Polym. Sci., 64:883 (1997) (no month avail.)
Y.B.J. Aldenhoff et al., Biomaterials, 18:167 (1997) (no month avail.)

*Primary Examiner*—Bernard Pianalto
*Attorney, Agent, or Firm*—Birch, Stewart, Kolasch & Birch, LLP

[57] ABSTRACT

There is disclosed a method for producing polymer articles having highly functionalized surfaces excellent in biocompatibility, by irradiating the surfaces of a polymer article with an ultraviolet laser beam in a solution containing a biopolymer. According to this method, a polymer article that has surfaces with biocompatibility, can be produced.

19 Claims, 2 Drawing Sheets

METHOD FOR PRODUCING POLYMER ARTICLES WITH A SURFACE MODIFIED

FIELD OF THE INVENTION

The present invention relates to a method for producing polymer articles having surfaces excellent in biocompatibility. More specifically, the present invention relates to a method for forming surfaces excellent in biocompatibility, by irradiating the surfaces of a polymer article, which are in contact with a biopolymer solution, with an ultraviolet laser beam, thereby causing a photoreaction to take place, to produce active species on the surfaces of the article, and immobilizing the biopolymer on the article surfaces through a reaction between the active species and the biopolymer.

BACKGROUND OF THE INVENTION

The processing of the surfaces of organic materials represented by polymer materials, for example, using an excimer laser that oscillates high-intensity pulsed light in the ultraviolet region, is under active study as precision surface processing and precision surface machining of organic materials, from both basic and application points of view.

On the other hand, to improve the biocompatibility of the surfaces of polymer articles used for artificial internal organs, sensors, etc., in the medical field is an important subject for improvement of the lifetime and reliability of implant-type artificial internal organs and implant-type sensors. Various investigations have been made so far, but under present conditions, practically endurable effective processing techniques have not yet been found. This is because various properties needed for artificial internal organs and sensors, such as mechanical strength (toughness) and durability, tend to be incompatible with biocompatibility. That is, polymer materials excellent in biocompatibility (e.g. biopolymers) are often low in mechanical toughness and cannot be used as articles. On the other hand, polymer materials excellent as articles are inferior in biocompatibility and therefore cannot be implanted as medical materials in the body for a long period of time.

Accordingly, under present conditions, materials having both properties to a certain extent are currently used, tentatively. Under these conditions, a conceivable method for improving biocompatibility of the surfaces of polymer articles is to chemically coat the surfaces of an article excellent in mechanical toughness with a substance excellent in biocompatibility. Since biocompatibility depends on surface properties, by coating the surface thinly with a substance excellent in biocompatibility through chemical bonds between the surface and the substance, the biocompatibility of an article can be improved without detriment to the other properties of the article.

Kaetsu reported a method for immobilizing polysaccharides on the surfaces of a polymer article by irradiating the polymer article with light from an ultraviolet lamp in an aqueous solution of a mixture of polysaccharides and a photopolymerization initiator, to initiate a crosslinking reaction by the initiator (Nucl. Instr. and Meth. in Phys. Res., Vol. B105, p 294 (1995)). This method is successful in immobilizing polysaccharides that are one type of biopolymers excellent in biocompatibility on the surfaces of an article, to improve the biocompatibility of the surfaces of the article. However, since, in this method, the crosslinking reaction by the photopolymerization initiator takes place randomly in solution, the thickness of the film of the polysaccharides immobilized on the article surfaces becomes increased, leading to the disadvantages that the mechanical properties of the article are lowered, and that the photopolymerization initiator inevitably remains in the modification layer as impurities.

The present inventors proposed methods for effectively modifying the surfaces of a polymer article by ultraviolet laser processing (JP-A-4-183873 ("JP-A" means unexamined published Japanese patent application), JP-B-7-5775 ("JP-B" means examined Japanese patent publication), and JP-B-7-5777). With these methods, it is found out that, for instance, since active species are produced on the surfaces of an article by irradiation with a laser, an organic compound having a functional group, such as an azide group, a vinyl group, and an acetylene group, can be introduced on the surfaces of the article, to react with the active species on the surface, so that the organic compound can be immobilized through chemical bonds on the article surfaces irradiated with the laser beam. According to these methods, an organic compound, different from those constituting the article can be immobilized onto the surface of the article, without using photopolymerization initiators that will become an impurity.

SUMMARY OF THE INVENTION

An object of the present is to provide a method for producing a polymer article having surfaces excellent in biocompatibility.

Another object of the present invention is to provide a method, for processing the surfaces of a polymer article, that can form on the surfaces a modified layer that is very thin, that is free from impurities, and that is excellent in biocompatibility.

Other and further objects, features, and advantages of the invention will appear more fully from the following description, taken in connection with the accompanying drawings.

DETAILED DESCRIPTION OF THE INVENTION

Figure 1:
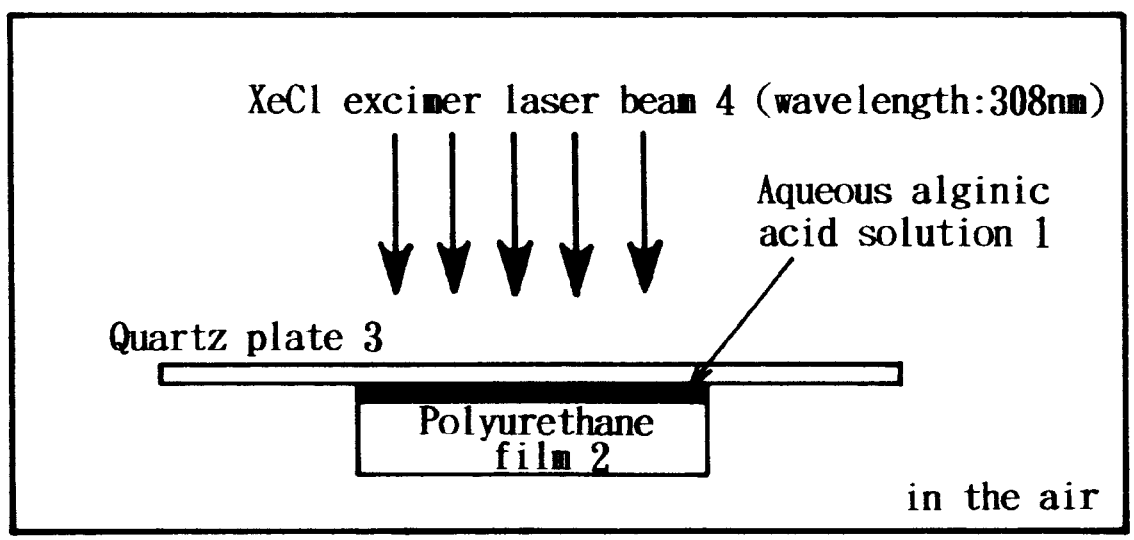
FIG. 1 is a schematic view of an XeCl excimer laser irradiation apparatus used in Examples of the present invention.

The present inventor, having investigated intensively to attain the above objects, have found that, when the surfaces of a polymer article are brought in contact with a solution of a biopolymer, such as an alginic acid solution, and the contact surface thereof is irradiated with a high-intensity ultraviolet laser beam, which is not absorbed by the solution, to cause a photoinduced reaction, the biopolymer is chemically immobilized onto the surfaces of the polymer article and the surfaces are modified, leading to the completion of the invention based on these findings.

That is, the present invention provides:

(1) A method for producing polymer articles whose surfaces are modified, comprising bringing surfaces of a polymer article in contact with a solution of a biopolymer and irradiating the contact surface of the solution of a biopolymer with an ultraviolet laser beam, to induce a photoinduced reaction, to immobilize the biopolymer molecule onto the surfaces of the article through chemical bonds;

(2) The method for producing polymer articles as stated in the above (1), wherein the ultraviolet laser beam is an excimer laser beam; and (3) The method for producing polymer articles as stated in the above (1) or (2), wherein the biopolymer is selected from among polysaccharides, proteins, or biomembrane substances.

In the present invention, the term "a biopolymer" means a protein, a nucleic acid, a polysaccharide, and the like. Preferable examples thereof that can be used include polysaccharides, such as alginic acid and dextrin; proteins, such as a polypeptide; or those substances having excellent compatibility with organism, such as biomembrane substances. Further, in the present invention, the solvent in which the biopolymer is dissolved is not particularly restricted, and preferably it is a substance that has no absorption at the ultraviolet laser wavelength to be used and that is hardly photo-decomposed when irradiated with ultraviolet light. Examples thereof include water, fluorinated alkane compounds, alkane compounds, ethers, and alcohols. The concentration of the biopolymer in the solution is not particularly restricted, as long as the concentration allows the laser beam to reach the article surfaces, and preferably the concentration is in the range of 0.01 to 40% by weight, and more preferably 0.5 to 10% by weight.

In the method of the present invention, specifically, the method for bringing the solution of a biopolymer in contact with the surfaces of a polymer article at the time when radiation of an ultraviolet laser beam is carried out, may be carried out in any way, and it is generally carried out in such a manner that the polymer article is immersed in the solution of a biopolymer, and the ultraviolet laser beam is irradiated from the liquid surface of the biopolymer solution. Use can also be made of a method in which the polymer article is coated or sprayed with the biopolymer solution, and the solution is irradiated with the ultraviolet laser beam.

The process of the photoreaction by the laser irradiation can be explained as follows. When the polymer article in the solution containing a biopolymer is irradiated with an ultraviolet laser beam, active species, such as radicals, are formed on the surfaces of the article by the photolysis of the surface layer. The ultraviolet laser beam employed is high-intense one sufficient to form the active species. In this time, it is necessary to select a laser beam whose wavelength is not adsorbed by the solution. Thus the solute and the solvent do not undergo a reaction due to the radiation of the laser beam, and active species are produced on the article surfaces with high efficiency. Since these active species are high in chemical reactivity, they react with the biopolymer immediately, and the biopolymer is immobilized on the surfaces. Differing from the reaction between active species and monomer molecules in the prior inventions of the present inventor (e.g. JP-B-7-5775), since the reaction in the present invention occurs between the active species present on the article surfaces and the polymer chains of the solute, only one photo-reaction makes polymer chains that are long molecules immobilized onto the surface. Therefore, it can be understood that the rate of the immobilization of the present invention is drastically improved.

Since the ultraviolet laser beam can strike a substrate with high intensity, the above photolysis reaction can be carried out efficiently with a pulse laser beam. In the method of the present invention, desirably the intensity of the ultraviolet laser light is lower than the threshold value intensity that causes ablation, and it is preferably about 0.1 to 200 mJ/cm$^2$/pulse, and more preferably 2 to 50 mJ/cm$^2$/pulse.

The immobilization of a biopolymer onto the surfaces of an article by the surface processing method of the present invention can be confirmed and quantitatively determined by measuring the processed film formed by the laser processing, for example, by reflection infrared absorption spectrometry or staining analysis.

Since organic materials like those polymer articles whose surfaces have been modified by immobilization of a biopolymer by irradiation with a laser beam, are made to have only the surface layers highly functionalized (e.g. given biocompatibility) while retaining the properties of the bulk, they can be used widely, for example, as medical materials and plates for the proliferation of cells, making use of these advantages of the materials. For example, alginic acid, a biopolymer, is excellent in biocompatibility, and therefore an article on whose surfaces alginic acid has been immobilized is readily compatible with living organisms and is a polymer article that is not likely to cause rejection symptoms.

Further, the present invention allows only a desired part on a polymer film to be subjected to surface processing by irradiating the part, where the modification is desired on the polymer film, with a laser beam that has been passed through a mask (e.g. a metal plate pattern), the mask corresponding to the part. On the other hand, in comparison with the beam size of other lasers, such as a helium-neon laser, an argon and krypton ion laser, and an Nd+:YAG laser, the beam size of an excimer laser is large in beam shape, it can produce large amounts of active species, and therefore it can process a large area easily. Particularly, in the present invention, since the nonthermal photochemical reaction by the ultraviolet laser beam can produce active species on the surfaces of an article, surface processing can be carried out very effectively.

As the laser in the present invention, an ultraviolet laser that can oscillate ultraviolet light corresponding to the absorption band of the polymer article is suitable, and the wavelength is preferably 400 nm or less. Above all, for example, an excimer laser and a dye laser are preferable, and particularly an ArF (wavelength: 193 nm), KrF (248 nm), XeCl (308 nm), or XeF (351 nm) excimer laser is appropriate. Further, one wherein light having the fundamental wavelength of a Nd+:YAG laser, a dye laser, a Kr ion laser, an Ar ion laser, or a copper vapor laser is converted to higher harmonics in the ultraviolet light region of 400 nm or less by a nonlinear optical device; a semiconductor laser, etc., are effective. The fluence of the laser varies depending on the type of polymer, but a high-intensity laser of about 0.1 mJ/pulse or more, with the pulse duration being about one or some nanoseconds, is desirable.

Herein, the polymer article refers to materials having a shape such as films, sheets, fibers, fiber-reinforced resins, and resin articles, and they are not necessarily articles that are final products, and the shape thereof is not restricted. The particular resin may be either amorphous or crystalline, and either aromatic or nonaromatic. The resin may be either a hydrocarbon resin or a fluororesin, or the resin may be a co-condensation polymer of these, or it may be a synthetic resin made of a mixture of the above. Further, the surface of a copolymer of a fluororesin and a hydrocarbon monomer can be similarly functionalized. Preferable resins include polyurethanes, polycarbonates, polyesters, polyimides, polyamide(nylon) resins, polyethylenes, polypropylenes, polysulfones, polysulfides, silicone resins, acrylic resins, methacrylic resins, etc.

The present invention resides in that a polymer article is irradiated with an ultraviolet laser beam in a solution containing a biopolymer, such as saccharides and proteins, to produce active species on the surfaces of the article, in an environment with side reactions suppressed, thereby causing the active species and the biopolymer to react with each other, to immobilize the biopolymer onto the article surfaces with high efficiency.

According to the method of the present invention, since highly reactive active species can be produced on the surfaces of a polymer article with high efficiency in a high purity using an ultraviolet laser beam, the surfaces of an organic material can be processed by the reaction of the active species and a biopolymer, to provide quite effective, precise, uniform and highly functionalized surfaces that are excellent in biocompatibility. In the present invention, since only the surface layer of an article reacts specifically with a biopolymer, the article surfaces can be improved in biocompatibility without damaging the properties of the article itself. The present invention has such features as that the modified layer is very thin, and that the mechanical properties of the article are not damaged, since the solution does not contain impurities, such as a photopolymerization initiator, and the reaction for the immobilization of a biopolymer is limited to the reaction with the article surfaces.

Now the present invention is described in more detail based on Examples, which are not meant to limit the present invention.

EXAMPLES

Example 1

Figure 2:
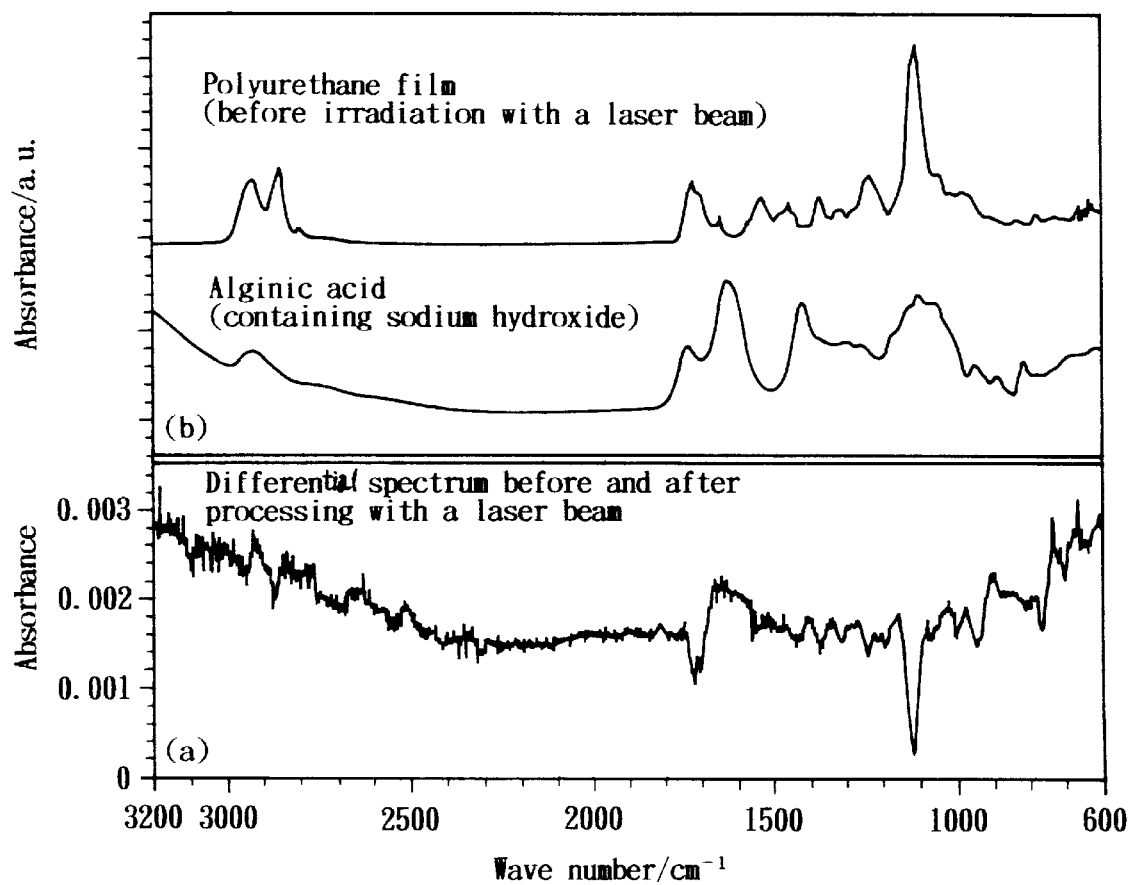
FIG. 2 shows, in (a), the differential reflection infrared adsorption spectrum of a polyurethane film subjected to a laser processing in Example 1 and, in (b), the reflection infrared adsorption spectra of a polyurethane film and alginic acid (shown for reference).

Using the apparatus shown in FIG. 1, a polyurethane film 2 in a 4% by weight aqueous alginic acid solution 1 (that contained 0.5% by weight of sodium hydroxide, in order to increase the solubility of alginic acid; the molecular weight of alginic acid being about 240,000) was irradiated at room temperature with 600 pulses of an XeCl excimer laser beam 4 (wavelength: 308 nm) at 40 mJ/cm$^2$/pulse through a quartz plate 3. As a result, the contact angle of water on the film surface decreased from 110 degrees to 60 degrees. It was found that the surface was made hydrophilic by alginic acid, since the contact angle was decreased only to 90 degrees when irradiation was carried out in the air or in water free from alginic acid. It was expected that, since alginic acid is one of saccharides having carboxylic acid groups as hydrophilic groups, alginic acid would be chemically immobilized in the surface processing by a laser beam. To confirm this, reflection infrared absorption spectrometry of the film subjected to the laser processing was carried out. The immobilization of alginic acid on the polyurethane film surfaces could be clearly identified from the differential spectrum measurement of (a) in FIG. 2. In FIG. 2, (b) shows absorption spectra of a polyurethane and alginic acid, for reference and comparison.

Further, to quantitatively determine alginic acid immobilized on the surfaces, staining analysis was carried out using a dye (Rhodamine 6G, trade name) capable of specifically being adsorbed to carboxylic acids, and it was found that alginic acid was immobilized on the film surfaces at a rate of about $3 \times 10^{11}$ molecules/cm$^2$. Since this corresponded to a surface layer thickness of about 1 nm, it was demonstrated that the modified layer of the polymer was quite thin, and modified surfaces excellent in biocompatibility were obtained without lowering the properties of the article itself.

Example 2

Using the apparatus shown in FIG. 1, a polycarbonate film in a 4% by weight aqueous alginic acid solution (that contained 0.5% by weight of sodium hydroxide, in order to increase the solubility of alginic acid) was irradiated at room temperature with 600 pulses of an XeCl excimer laser beam at 20 mJ/cm$^2$/pulse. As a result, the contact angle of water on the film surface decreased from 100 degrees to 50 degrees. Further, to quantitatively determine alginic acid immobilized on the surfaces, staining analysis was carried out using a dye (Rhodamine 6G) capable of specifically being adsorbed to carboxylic acids, and it was found that alginic acid was immobilized on the film surfaces at a rate of about $10^{11}$ molecules/cm$^2$.

Example 3

Using the apparatus shown in FIG. 1, a polyurethane film in a 5% by weight aqueous polysaccharide (xanthan gum) solution was irradiated at room temperature with 600 pulses of an XeCl excimer laser beam at 40 mJ/cm$^2$/pulse. As a result, the contact angle of water on the film surface decreased from 100 degrees to 75 degrees.

Comparative Example

It was attempted to modify the surfaces of a polyurethane film in the same manner as in Example 1 using the alginic acid solution and the irradiation apparatus shown in FIG. 1, except that, as an irradiation laser beam, a near infrared laser beam (YAG laser beam fundamental waves; wavelength, 1064 nm) was used, but the contact angle of the surface remained the same before and after the irradiation with the laser beam, and it was found that alginic acid was not immobilized on the surfaces.

Having described our invention as related to the present embodiments, it is our intention that the invention not be limited by any of the details of the description, unless otherwise specified, but rather be construed broadly within its spirit and scope as set out in the accompanying claims.

What I claim is:

1. A method for producing polymer articles whose surfaces are modified, comprising bringing surfaces of a polymer article in contact with a solution containing a biopolymer and not containing a photopolymerization initiator and irradiating the contact surface of the solution containing the biopolymer with an ultraviolet laser beam having sufficient intensity for forming active species on the surface of the polymer article, to induce a photoinduced reaction, to chemically immobilize the biopolymer in the solution onto the surfaces of the article.

2. The method for producing polymer articles as claimed in claim 1, wherein the ultraviolet laser beam is an excimer laser beam.

3. The method for producing polymer articles as claimed in claim 1, wherein the biopolymer is selected from the group consisting of polysaccharides, proteins, and biomembrane substances.

4. The method for producing polymer articles as claimed in claim 1, wherein the irradiation of the ultraviolet laser beam is carried out by, after immersing the polymer article in the solution of a biopolymer, or spraying or coating the polymer article with the solution of a biopolymer, irradiating the solution surface of the solution of a biopolymer with the ultraviolet laser beam.

5. The method for producing polymer articles as claimed in claim 1, wherein the intensity of the ultraviolet laser light is about 0.1 to 200 mJ/cm$^2$/pulse.

6. The method for producing polymer articles as claimed in claim 5, wherein the intensity of the ultraviolet laser light is about 2 to 50 mJ/cm$^2$/pulse.

7. The method for producing polymer articles as claimed in claim 1, wherein the biopolymer is selected from the group consisting of proteins, nucleic acids, polysaccharides, and combinations thereof.

8. The method for producing polymer articles as claimed in claim 7, wherein the polysaccharides are selected from the group consisting of alginic acid and dextrin.

9. The method for producing polymer articles as claimed in claim 1, wherein the biopolymer is dissolved in a solvent which is a substance that has no absorption at the ultraviolet laser wavelength which is used and which is hardly photo-decomposed when irradiated with ultraviolet light.

10. The method for producing polymer articles as claimed in claim 9, wherein the solvent is selected from the group consisting of water, fluorinated alkane compounds, alkane compounds, ethers and alcohols.

11. The method for producing polymer articles as claimed in claim 1, wherein the concentration of the biopolymer in the solution is present in an effective amount so as to allow the laser beam to reach the article surface.

12. The method for producing polymer articles as claimed in claim 11, wherein the concentration of the biopolymer in the solution is in the range of 0.01 to 40% by weight.

13. The method for producing polymer articles as claimed in claim 11, wherein the concentration of the biopolymer in the solution is in the range of 05 to 10% by weight.

14. The method for producing polymer articles as claimed in claim 1, wherein the wavelength of the ultraviolet laser beam is 400 nm or less.

15. The method for producing polymer articles as claimed in claim 1, wherein the laser is an excimer laser or a dye laser.

16. The method for producing polymer articles as claimed in claim 15, wherein the laser is an ArF laser having a wavelength of 193 nm, an KrF laser having a wavelength of 248 nm, an XeCl laser having a wavelength of 308 nm or an XeF laser having a wavelength of 351 nm.

17. The method for producing polymer articles as claimed in claim 1, wherein the polymer articles comprise a resin which is either amorphous or crystalline, and either aromatic or nonaromatic.

18. The method for producing polymer articles as claimed in claim 17, wherein the resin is either a hydrocarbon resin or a fluororesin, or the resin is a co-condensation polymer of a hydrocarbon resin and a fluororesin, or the resin is a synthetic resin made of a mixture of a hydrocarbon resin and a fluororesin.

19. The method for producing polymer articles as claimed in claim 18, wherein the resin is selected from the group consisting of polyurethanes, polycarbonates, polyesters, polyimides, polyamide (nylon) resins, polyethylenes, polypropylenes, polysulfones, polysulfides, silicone resins, acrylic resins and methacrylic resins.

* * * * *